United States Patent [19]

Marne

[11] 4,213,208
[45] Jul. 22, 1980

[54] METATARSO-PHALANGEAL JOINT IMPLANT

[76] Inventor: Sheldon Marne, 10631 NW. 29 Ct., Sunrise, Fla. 33322

[21] Appl. No.: 857,786

[22] Filed: Dec. 5, 1977

[51] Int. Cl.² ............................................. A61F 1/24
[52] U.S. Cl. .................................... 3/1.91; 128/92 C
[58] Field of Search ............................. 3/1.91–1.913; 128/92 C, 92 CA

[56] References Cited

U.S. PATENT DOCUMENTS

| | | | |
|---|---|---|---|
| 3,506,982 | 4/1970 | Steffee | 3/1.91 |
| 3,739,403 | 6/1973 | Nicolle | 3/1.91 |
| 3,805,302 | 4/1974 | Mathys | 3/1.91 |
| 3,886,600 | 6/1975 | Kahn et al. | 3/1.91 |
| 4,011,603 | 3/1977 | Steffee | 3/1.91 |

*Primary Examiner*—Ronald L. Frinks
*Attorney, Agent, or Firm*—Barry L. Haley

[57] ABSTRACT

An endoprosthetic metatarso-phalangeal replacement joint permitting dorsi and plantar flexion with minimal medial and lateral motion and true ginglymus motion. The device includes a male joint member that is surgically implanted in the proximal phalangeal base, the male member including a metallic cylinder connected to a tissue-inert plastic intramedullary stem, the cylinder having inert material embedded therein integrally coupled to said stem forming a drum-shaped head. The embedded inert material walls at each end of the head are recessed. The female joint member includes a molded, tissue-inert plastic intramedullary stem integrally formed with a socket having a partially cylindrical wall of a predetermined arcuate length relative to the axis longitudinally of the intramedullary stems that receives the drum-shaped head of the male joint member. The socket side walls include axially aligned conical protuberances that are received in the recessed walls of the drum-shaped head when male and female members are joined. A hemispherically shaped, elastic shield fits over the joint head and socket when engaged and is tapered so as to not become impinged when dorsi flexion within the foot is experienced. The intramedullary stems are longitudinally axially aligned with the axial rotation center of the head and socket. The device may be utilized as a replacement joint for either the hallux or the lesser metatarso-phalangeal joints.

3 Claims, 18 Drawing Figures

METATARSO-PHALANGEAL JOINT IMPLANT

BACKGROUND OF THE INVENTION

This invention relates generally to an endoprosthetic device which allows for total replacement of the metatarso-phalangeal joint of a human being, and specifically, to a replacement joint which most closely imitates the human metatarso-phalangeal joint. The device is implanted in the hollowed out intramedullary space in the bone ends.

A search of the prior art shows a dearth of replacement devices for the human metatarso-phalangeal joint, and those which do exist, have several deficiencies, the primary deficiency being that, once implanted, are deleteriously affected by certain stresses placed upon the foot. Another deficiency is that prior art devices do not provide for total joint movement that closely assimulates an actual human joint. The actual human joint is constructed by nature to provide motion in three planes about the joint, which includes dorsi flexion of 90 degrees, a plantar flexion of from 45 to 60 degrees, medial deviation from 1 to 5 degrees, and lateral deviation from 1 to 5 degrees, while at the same time directly bearing weight. The prior art deficiencies have resulted in fracture of the stem, fracture of the hinge, and rotation of the joint in the intramedullary canal. These deficiencies greatly restrict a patient's movement and activities, preventing the patient from returning to a normal state.

The present invention overcomes deficiencies found in the prior art by providing an artificial metatarsophalangeal joint which may be used to replace the human joint and which provides for a weight bearing joint which is essential for the proper motion of the person in conjunction with a sturdy and reliable joint that is capable of duplicating the motion and withstanding the forces encountered as in a normal human metatarso-phalangeal joint.

BRIEF SUMMARY OF THE INVENTION

An endoprosthetic device for providing an artificial joint to replace the metatarso-phalangeal joint in a human being comprising male and female joint members which are surgically implanted in the intramedullary bone canal and snapped together. The male member includes a metallic cylinder coupled to a stem having an intramedullary shaft, the stem and shaft, consisting of a tissue-inert plastic material. The cylinder includes plastic-inert material embedded therein formed integrally with the stem, the end walls of the cylinder including recessed portions. The stem connects the medullary shaft to the cylinder through an aperture in the cylinder and acts as a stop for movement of the joint as is explained in greater detail below.

The female member is constructed of a tissue-inert plastic material and includes a socket and a medullary shaft separated by an intermediate disc that limits the penetration of the medullary shaft. The socket includes a partially cylindrical wall of a predetermined arcuate length as a function of and relative to the longitudinal axis of the stem and medullary shaft. The side walls of the socket include conically shaped protuberances which are aligned along the central axis of the socket cylindrical wall which is the axis of rotation of the joint. The socket protuberances are sized to fit within the recessed wall portions of the male member cylindrical head without engaging the recessed walls except as to prevent disengagement of the male and female members.

The male member, stem and shaft longitudinal axis is aligned with the central axis of the drum-shaped head formed by the cylinder and embedded material such that when the male and female members of the joint are engaged, the stem and medullary shafts of each member can be disposed in longitudinal axial alignment about the center of rotation of the joint. The arcuate length of the socket cylindrical wall is sized relative to the longitudinal axis of the stem and medullary shaft of the female member and the stem thickness of the male member to allow for dorsi flexion of 90 degrees and plantar flexion of from 45 to 60 degrees. The socket side walls are spaced and sized relative to the drum-shaped head of the male member to allow medial deviation from one to five degrees and lateral deviation from one to five degrees.

A resilient tissue-inert cap which is somewhat hemispherically shaped, is connected to the male member and encompasses the socket to protect the joint engagement, the cap being shaped to prevent inpingement or hinder normal joint movement.

The medullary shaft on each member may include at least one raised flanged portion which acts to prevent rotation of the shafts within the medullary canals of bone once implanted therein.

The cross-sectional shape of the medullary shafts are such as to prevent rotation of either joint member once it has been surgically implanted. The joint is implanted by placing the male member in the medullary canal and the female member and shaft in the bone medullary canal and then snapping the drum-shaped head into the socket. The resilient cap prohibits tissue growth that might otherwise interfere with the movement of the drum-shaped head and socket. Variations in the medullary shaft can be employed in various embodiments of the invention to accommodate implantation in either the hallux or the lesser metatarso-phalangeal joints.

It is an object of this invention to provide a metatarso-phalangeal joint prosthesis that can be easily implanted in a patient and which can be inserted as two individual subsections and snapped together as a stable joint.

It is another object of this invention to provide a joint prosthesis for the metatarso-phalangeal joint which can be capable of receiving direct weight while still providing normal joint motion comparable to an actual healthy human joint.

And yet, still another object of this invention is to provide a metatarso-phalangeal joint prosthesis which is noncomplex in design and can be relatively inexpensively manufactured.

In accordance with these and other objects which will be apparent hereinafter, the instant invention will now be described with particular reference to the accompanying drawings.

PREFERRED EMBODIMENT OF THE INVENTION

Figure 1:
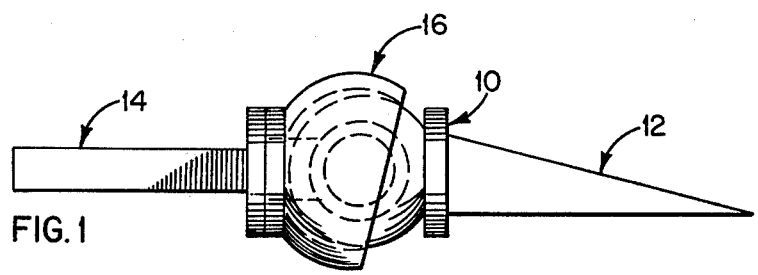
FIG. 1 shows a side elevational view of the instant invention.
Figure 2:
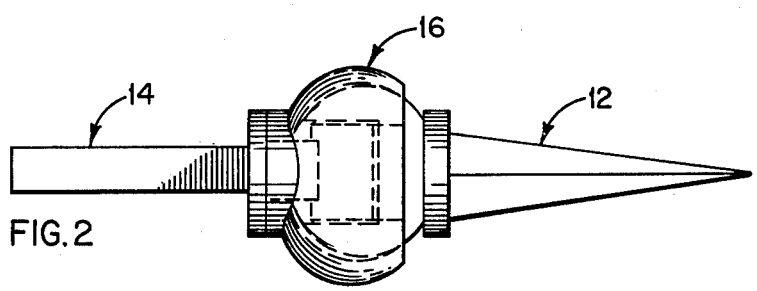
FIG. 2 shows a top plan view of the instant invention.
Figures 3, 7:
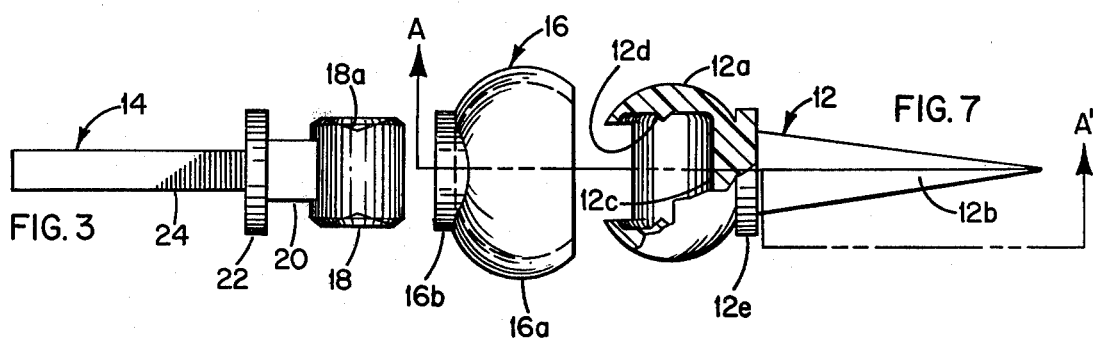
FIGS. 3 and 7 show a top plan exploded view of the instant invention.
Figures 4, 8:
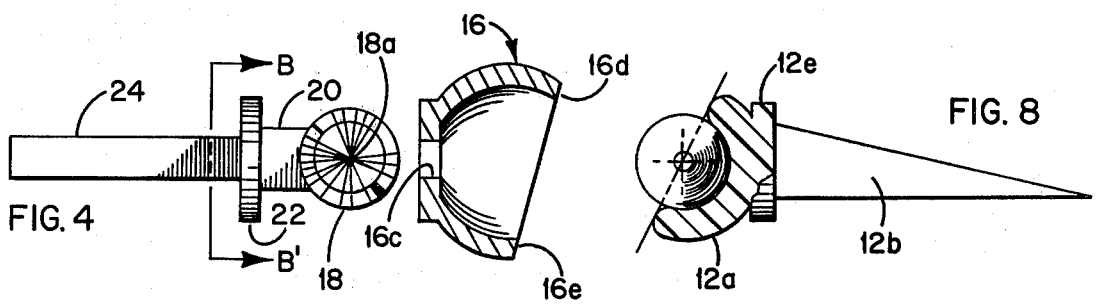
FIGS. 4 and 8 show a side elevational exploded view of the instant invention.
Figure 5:
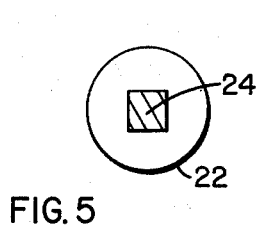
FIG. 5 shows an elevational cross-sectional view through line B—B' shown in FIG. 4.
Figure 6:
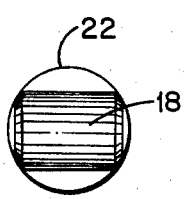
FIG. 6 shows an end elevational view of the male element of the instant invention.
Figure 9:
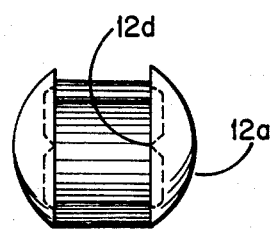
FIG. 9 shows an end elevational view of the socket in accordance with the instant invention.
Figure 10:
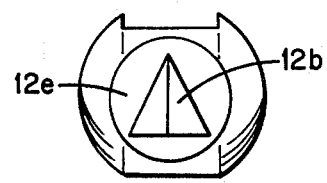
FIG. 10 shows an end elevational view of the opposite end of the female member of the instant invention.
Figure 11:
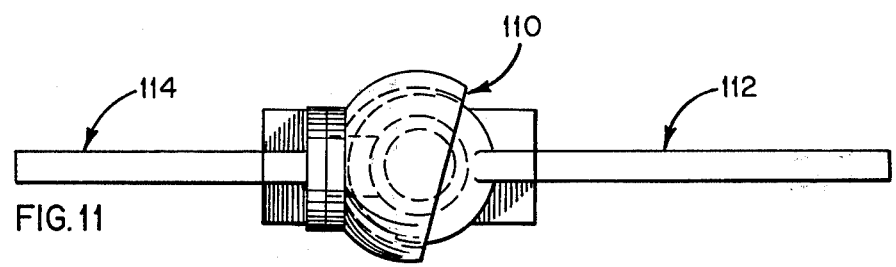
FIG. 11 shows a side elevational view of an alternate embodiment of the instant invention.
Figure 12:
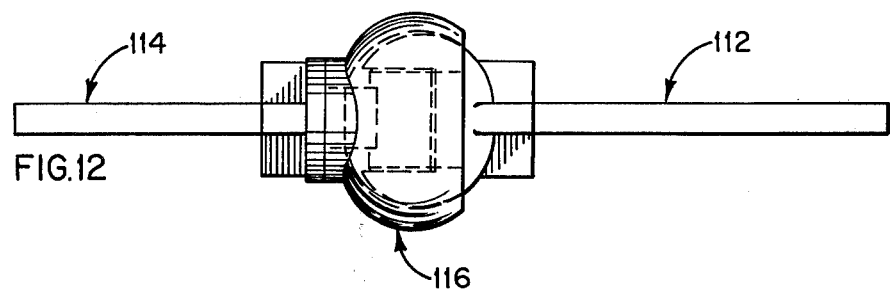
FIG. 12 shows a top plan view of the alternate embodiment of the instant invention.
Figures 13, 16:
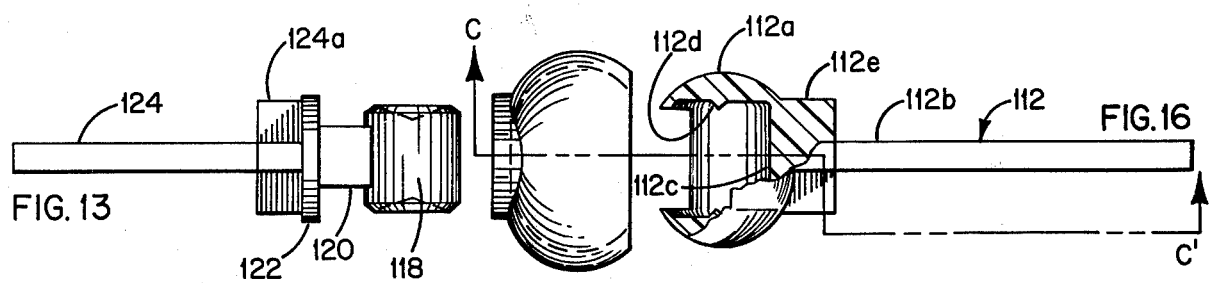
FIGS. 13 and 16 show an exploded top plan view of the alternate embodiment of the instant invention.
Figures 14, 17:
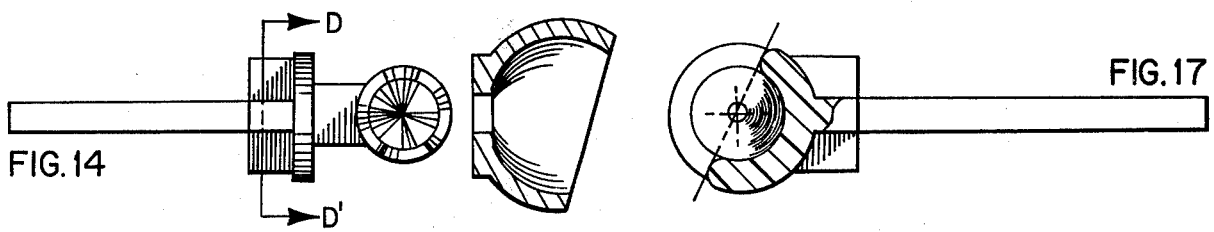
FIGS. 14 and 17 show a side elevational view of an alternate embodiment in accordance with the instant invention.
Figure 15:
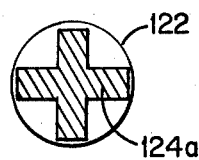
FIG. 15 shows a cross-sectional elevational view along line D—D' shown in FIG. 14.
Figure 18:
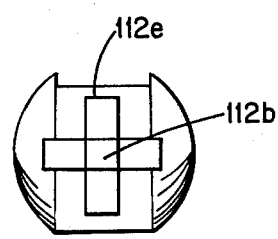
FIG. 18 shows an end elevational view of the female member showing an alternate embodiment of the invention.

Referring now to the drawings, FIGS. 1 through 10 shows a replacement joint for the hallux shown generally at 10 comprised of a female member 12 which includes a socket 12c engaged with a male joint member 14 and a protective flexible cap 16 being disposed over the joint. The protective flexible cap prevents surrounding tissue growth after implantation from interferring with the relative movement and operation of the joint. Referring to FIGS. 3 and 7, the female joint member 12 includes a hemispherically-shaped end 12a having a partially cylindrically shaped socket 12c. A pair of protuberances 12d extend inwardly from opposite walls of the socket 12c in the direction of the cylindrical axis of the socket, which is the axis of rotation of the entire joint. A disc-shaped intermediate barrier 12e is integrally formed with the socket head 12a and medullary shaft 12b.

The male joint member 14 includes a metallic cylinder 18 mounted on stem 20 received through an aperture in the cylinder 18. A medullary shaft 24, disc shaped barrier 22 and material embedded in cylinder 18 are integrally formed of a tissue-inert plastic material. The cylinder, which is metallic, may be made of stainless steel or the like. The portion of the stem 20 embedded in cylinder 18 includes recessed walls 18a that are larger and deeper than the height of protuberances 12 at the axial center of cylinder 18. The distance between the end tips of the protuberances is less than the height of cylinder 18 such that once the male and female joint members are snapped together, the protuberances prevent disengagement of the joint, while still allowing some slight degree of lateral and medial movement.

The upper and lower surfaces of stem 20 act as a stop for dorsi and plantar flexion of the joint by engaging the ends of the partially cylindrical wall 12a of socket 12c. The socket wall 12a arcuate length is determined to provide a 90 degree relative movement upward (dorsi flexion) between the male and female medullary shafts and from 45 degrees to 60 degrees downward (plantar flexion) movement as measured from a horizontal line.

The intermediate discs 22 and 12e formed on the male and female joint members respectively act as barriers that engage the bone faces to limit medullary penetration of shafts 24 and 12b respectively after implantation. Shaft 12b is triangularly shaped in cross-section to firmly fit within the medullary canal of the hallux metatarsal bone while shaft 24 is rectangular to firmly fit in the phalangeal bone, both shapes preventing rotation of the joint members.

In an alternate embodiment shown in FIGS. 11 through 18, a metatarso-phalangeal prosthesis is shown for implantation in the lesser metatarso-phalangeal joint. The socket 112c and male member cylindrical head 118 and stem 120 function as described above. In this embodiment, however, the medullary shaft 124 which engages the phalangeal medullary canal, includes at least one raised wall 124a coupled adjacent intermediate disc 122 which acts as a barrier, the flanged wall 124a penetrating the bone to prevent rotation of male member 114. Likewise, on the female member, at least one raised wall 112e which is intregally formed with the socket head 112a is disposed at the end of medullary shaft 112b to engage the bone to prevent rotation of the female member. As shown in this embodiment, the rotation preventing walls 124a are formed as a cross. The protective cap 116 fits and is mounted on stem 120 through an aperture in the cap and is used to cover and protect the joint as described above.

When considering either embodiment described above, it should be realized that the longitudinal axes of the medullary shafts of both the male and female members when joined are aligned to intersect the center of rotation of the joint which is at the axial center of the cylinder mounted on the male member and the cylindrical axis of the socket whih provides the proper relationship for the metatarso-phalangeal joint. The cylinder 18 shown in FIG. 3 and cylinder 118 shown in FIG. 13, includes an annular lip at each end which allows for their relative movement (when disposed within the plastic socket) between the metal and plastic surfaces to prevent contact between the embedded plastic material and the plastic socket. This insures metal to plastic joint engagement. The open portion of cap 16 is cut at an angle relative to the center of rotation to correspond to the arcuate length of the partial cylindrical wall of socket 12a so that the flexible cap does not impinge relative movement between the male and female members of the joint.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A metatarso-phalangeal joint prosthesis comprising;

a male joint member, said male joint member including a medullary shaft, a stem integrally connected to said shaft and a metallic cylinder coupled to said stem, said stem and shaft consisting of a tissue-inert material, a portion of said stem being embedded within said cylinder, said embedded portion within said cylinder having and forming recessed walls within said cylinder, said shaft and stem longitudinal axis intersecting the longitudinal axis of said cylinder;

a female member, said female member having a medullary shaft disposed adjacent one end and integrally formed therein at the opposite end a socket, said socket having a partially cylindrical wall of a predetermined arcuate length, said socket being sized to receive said cylindrical head of said male member, said female member medullary shaft having a longitudinal axis that intersects the axis of said socket, said socket including at least one inwardly disposed protuberance, said protuberance being aligned along the axis of said socket;

said female member socket having an arcuate wall of a predetermined length which engages the stem on said male member to permit relative movement between the medullary shafts of the male and female members from a first position of ninety degrees to a second position between forty-five and sixty degrees which represents dorsi and plantar flexion;

a flexible cap coupled to and encapsulating said socket body, said cap being shaped so as to not be compressed while there is stress upon the joint in dorsi flexion, said cap being aligned with the stem and axis of rotation of the joint when connected; and said medullary shafts including at least one flange to prevent rotation of said joint.

2. A prosthetic device as in claim 1, wherein:

said male and female members include intermediately disposed barrier discs, said discs being integrally connected to said medullary shaft to act as a barrier to limit the penetration of said medullary shafts within a patient's bone.

3. A prosthetic device as in claim 1, wherein:

said male member cylinder height is sized to fit within said female member socket, the socket height being such relative to the cylinder height to allow one to five degrees medial motion and one to five degrees lateral motion between the medullary shafts of said male and female members.

* * * * *